United States Patent [19]

Pickart

[11] Patent Number: 5,059,588

[45] Date of Patent: Oct. 22, 1991

[54] METHODS AND COMPOSITIONS FOR HEALING BONE USING GLY HIS LYS: COPPER

[75] Inventor: Loren R. Pickart, Bellevue, Wash.

[73] Assignee: ProCyte Corporation, Incorporated, Redmond, Wash.

[21] Appl. No.: 421,101

[22] Filed: Oct. 13, 1989

[51] Int. Cl.$^5$ .................. A61K 37/02; C07K 5/10; C07K 7/10

[52] U.S. Cl. .......................... 514/12; 514/6; 514/18; 530/331; 530/336

[58] Field of Search ............... 514/18, 6, 12; 530/331, 530/356

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/177 |
| 3,767,784 | 10/1973 | Gluck | 424/28 |
| 3,832,338 | 8/1974 | Huber et al. | 260/113 |
| 4,022,888 | 5/1977 | Huber et al. | 424/177 |
| 4,167,945 | 9/1979 | Gottlieb | 128/334 R |
| 4,177,261 | 12/1979 | Dietze et al. | 424/101 |
| 4,263,428 | 4/1981 | Apple et al. | 536/17 A |
| 4,287,184 | 9/1981 | Young | 424/177 |
| 4,440,788 | 4/1984 | Terayama | 424/320 |
| 4,665,054 | 5/1987 | Pickart | 514/18 |
| 4,760,051 | 7/1988 | Pickart | 514/18 |
| 4,767,753 | 8/1988 | Pickart | 514/18 |
| 4,810,693 | 3/1989 | Pickart | 514/18 |
| 4,877,770 | 10/1989 | Pickart | 514/18 |
| 4,937,230 | 6/1990 | Pickart | 514/18 |

FOREIGN PATENT DOCUMENTS 0078228 4/1982 European Pat. Off. .
86/00222 1/1986 PCT Int'l Appl. .

OTHER PUBLICATIONS

Pickart et al., "Growth-Modulating Tripeptide (Glycylhistidyllysine): Association with Copper and Iron in Plasma and Stimulation of Adhesive and Growth of Hepatoma Cells in Culture by Tripeptide-Metal Ion Complexes," *J. Physiol.* 102(2):129–139, 1980.

Williams et al., "Glycyl-L-Histidyl-L-Lysine, A Growth Promoting Factor for Human Cells," *Cytobios* 27(105):19–25, 1980.

Mochida Parmaceutical Co., Ltd., "Anti-Inflammatory Injections Containing Superoxide Dismutase," Jpn. Kokai Tokkyo Koho, 81 07, 720, Jan. 27, 1981 (Cited in *Chem. Abstracts* 94:145386f, 1981).

Downey et al., "Acceleration of Wound Healing Using GHL-Cu(II)," *Surgical Forum* 36:573–575 (1985).

Pickart et al., "A Human Plasma Growth Factor with Superoxide Dismutase-Like and Wound-Healing Properties," Superoxide Dim. Chem., Biol. Med. Proc. Int. Conf. 4th 1985 (Pub. 1986), 555–557 (Cited in *Chem. Abstracts* 106:13579c).

Frater-Schroder et al., "Tumor Necrosis Factor Type a, A Potential Inhibitor of Endothelial Cell Growth In Vitro is Angiogenic In Vivo," *Proc. Natl. Acad. Sci. USA* 34:5277–5281 (1987).

"Newsreport on Use of GGH-Cu(II) and Ascorbic Acid," *Natural Healing Annual* 1986, p. 38, (M. Bricklin (ed.), Prevention Magazine, Rodale Press, Emmaus, Pa.).

Pickart et al., "A Synthetic Tripeptide Which Increases Survival of Normal Liver Cells, and Stimulates Growth in Hepatoma Cells," *Biochem. Biophys. Res. Commun.* 54(2):562–566, 1973.

Aonuma et al., "Studies on Anti-Ulcerogenic Protein in Inflamed Rabbit Skin Tissues," *Yakugaku Zasshi* 104(4):362–373, 1984.

(List continued on next page.)

*Primary Examiner*—Lester L. Lee
*Attorney, Agent, or Firm*—Seed and Berry

[57] ABSTRACT

A method of promoting and accelerating the healing of bones in animals utilizing an effective amount of a GHL-(Cu) pharmicuetical composition is disclosed. Also methods of inducing the formulation of granulation tissue in affected bones of animals using a GHL-(Cu) composition is disclosed.

16 Claims, 8 Drawing Sheets

OTHER PUBLICATIONS

Sorenson, "Copper Complexes: A Physiologic Approach to Treatment of Chronic Diseases," *Comprehensive Therapy* 11(4):49–64, 1985.

Pickart et al., "Inhibition of the Growth of Cultured Cells and an Implanted Fibrosarcoma by Aroylhydrazone Analogs of the Gly-His-Lys-Cu(II) Complex," *Biochem. Pharmacol.* 32(24):3868–3871, 1983.

Pickart et al., "Growth-Modulating Plasma Tripeptide May Function by Facilitating Copper Uptake into Cells," *Nature* 288:715–717, 1980.

Kwa et al., "PMR Studies of Cu(II) and Zn(II) Interaction with Glycyl-L-Histidyl-L-Lysine and Related Peptides," *Peptides: Structure and Function* 8:805–808, 1983.

Perkins et al., "The Structure of a Copper Complex of the Growth Factor Glycyl-L-Histidyl-L-Lysine at 1.1 A Resolution," *Inorganica Chimica Acta* 82:93–99, 1984.

Kimoto et al., "Enhancement of Antitumor Activity of Ascorbate Against Ehrich Ascites Tumor Cells by the Copper: Glycylglycylhistidine Complex," *Cancer Research* 43:824–828, 1983.

Poole et al., "Stimulation of Rat Peritoneal Mast Cell Migration by Tumor-Derived Peptides," *Cancer Research* 43:5857–5861, 1983.

Raju et al., "Ceruloplasmin, Copper Ions, and Angiogenesis," *JNCL* 69(5):1183–1188, 1982.

Freedman et al., "Structure of the Glycyl-L-Histidyl-L-Lysine-Copper(II) Complex in Solution," *Biochemistry* 21:4540–4544, 1982.

Kwa, "Glycyl-L-Histidyl-L-Lysine: Synthesis of Analogs and NMR Studies," Ph.D. Thesis, University of Washington, 1983.

Loker, "Synthesis of Blood Serum Peptide Cell Growth Factors," Ph.D. Thesis, University of Washington, 1980.

Pickart, "The Biological Effects and Mechanism of Action of the Plasma Tripeptide Glycyl-L-Histidyl-L-Lysine," *Lymphonkines* 8:425–446, 1983.

Pickart, "The Use of Glycylhistidyllysine in Culture Systems," *In Vitro* 17(6):459–466 (1981).

METHODS AND COMPOSITIONS FOR HEALING BONE USING GLY HIS LYS: COPPER

DESCRIPTION

Technical Field

This invention relates generally to the healing of bones, and more specifically, to metal-peptide complexes that are useful in promoting and accelerating the healing of bone and other hard tissue in warm-blooded animals.

BACKGROUND OF THE INVENTION

The mechanism and progress of bone healing in humans and other warm-blooded animals are often incomplete or proceed at an unacceptably slow pace. The initial mechanism for the healing of hard tissue (e.g., bone) may generally be characterized as a three-phase process.

The first phase of healing involves the recruitment of the proper types of white blood cells to cleanse the wound and initiate the healing response. To this end, the body seals off blood flow into the damaged area and a white cell type, called neutrophils, secrete toxic superoxide molecules into the area to kill bacteria and induce a general inflammation.

The second phase involves the formation of granulation tissue (i.e., a mixture of fibroblasts, macrophages, and new blood vessels in a loose matrix of collagen and other materials). During this stage of healing, the production of superoxide ion and the inflammatory response is suppressed, while macrophages invade to clean up tissue debris and open a path for mast cells and fibroblasts to follow and secrete angiogenic factors to attract capillary endothelial cells.

Monocytes are also involved, both to secrete fibroblast-activating factors and for conversion to macrophages. Mast cells serve as "helper cells" that amplify new capillary growth. In addition, there is a proliferation of fibroblasts and other cells that secrete the structural protein collagen into the area. There is a migration of chondrocytes and osteoblasts into the healing area to further synthesize bone structural materials.

The third and final stage involves the remodeling and formation of new connective tissue and bone components.

Although there have been a number of substances that are alleged to be capable of inducing cartilage and bone formation, there is a need in the art for compositions and methods which promote the healing of bone and other hard tissue in warm-blooded animals. The present invention provides such compositions and methods, and further provides other related advantages.

DISCLOSURE OF THE INVENTION

Briefly stated, the present invention provides metal-peptide complexes and derivatives thereof which promote the healing of affected bone and other hard tissue, such as cartilage, in warm-blooded animals. For purposes of the present invention, the term "affected bone" includes bone fractures, defects, injury or surgical alteration or implant.

More specifically, the present invention provides methods for promoting the healing of affected bone, for inducing the formation of granulation tissue in affected bone, and accelerating the formation of new bone growth associated with affected bone, such as the implantation of an artifical device in bone.

In addition, pharmaceutical compositions and devices containing the metal-peptide complexes and derivatives thereof which promote and accelerate the healing of bone and other hard tissue in warm-blooded animals are disclosed.

The metal-peptide complexes described herein include glycyl-L-histidyl-L-lysine:copper(II) (GHL-Cu), L-lysyl-L-histidyl-glycine:copper(II) (LHG-Cu), and various derivatives of GHL-Cu and LHG-Cu.

The derivatives of GHL-Cu have the general formula:

wherein R is selected from the group consisting of an $-NH_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-propyl-L-valyl-L-phenylalanyl-L-valine, L-valyl-L-phenylalanyl-L-valine, L-tryptophan, or $(glycyl)_n$-L-tryptophan, where $n=1-2$.

In addition to the derivatives described above, other chemical modifications may be made to alter the biological activity of GHL and GHL-Cu derivatives. For instance, glycine may be replaced by a variety of other small amino acids, including alanine, serine, and valine. Further, the copper(II) binding affinity of the molecule may be increased by addition of an N-terminal amino acid, such as glycine, to convert glycyl-L-histidyl-L-lysine to glycyl-L-glycyl-L-histidyl-L-lysine. In addition, glycine could be added to a derivative as described above to create the corresponding tetrapeptide. The binding affinity for copper(II) of the imidazole group in the histidyl residue may be modified by substitution of 3-methylhistidine for histidine or by extending the lysyl side chains by adding additional carbon atoms to the chain. Similarly, molecules may be added to GHL-Cu and derivatives thereof to form ternary complexes, for example, the addition of histidine, or other amino acids and imidazole ring compounds, to form a GHL-Cu-histidine complex.

The derivatives of LHG-Cu have the general formula:

wherein R is selected from the group consisting of an $-NH_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-propyl-L-valyl-L-phenylalanyl-L-valine or L-valyl, L-phenylalanyl-L-valine, L-tryptophan, or $(glycyl)_n$-L-tryptophan, where $n=1-2$.

In addition to the derivatives described above, other chemical modifications may be made to alter the biological activity of LHG and LHG-Cu derivatives. For instance, lysine may be replaced by a variety of other small amino acids, including alanine, serine, and valine.

Further, the copper(II) binding affinity of the molecule may be increased by addition of an N-terminal amino acid, such as glycine, to convert L-lysyl-L-histidyl-glycine to glycyl-L-lysyl-L-histidyl-glycine. In addition, glycine could be added to a derivative as described above to create the corresponding tetrapeptide. The binding affinity for copper(II) of the imidazole group in the histidyl residue may be modified by substitution of 3-methylhistidine for histidine or by extending the lysyl side chains by adding additional carbon atoms to the chain. Similarly, molecules may be added to GHL-Cu and derivatives thereof to form ternary complexes, for example, the addition of histidine, or other amino acids and imidazole ring compounds, to form a GHL-Cu-histidine complex.

Those skilled in the art will recognize that other metals could be substituted for copper yield active compositions for use in the methods of the present invention.

The methods of promoting the healing, inducing the formation of granulation tissue, and accelerating the formation of new bone growth associated with affected bone described herein generally comprise administering to the animal a therapeutically effective amount of one of the compositions described above in order to effect the desired purpose.

Other aspects of the present invention will become evident upon reference to the following detailed description and attached drawings.

BEST MODE FOR CARRYING OUT THE INVENTION

As described herein, GHL-Cu, LHG-Cu and derivatives thereof may be used in the promotion of healing of bone and other hard tissue in warm-blooded animals. The application of pharmaceutical preparations containing these compositions are useful in accelerating the formation of granulation tissue and the overall healing rate of bone. The compositions of the present invention are described in detail in U.S. Pat. Nos. 4,760,051; 4,665,054; and 4,810,693; which are incorporated herein by reference.

Within the present invention, one may utilize a ratio of GHL, LHG or a derivative thereof to copper of 1:1, 2:1, or less. However, within a preferred embodiment, optimal healing occurs with a ratio of 0.5-0.9 copper atoms per GHL or LHG molecule. Copper in molar excess of GHL or LHG (>1.00) is loosely bound and may inhibit rather than enhance bone healing.

Pharmaceutical preparations containing GHL-Cu, LHG-Cu and derivatives thereof may be in the form of either liquids, lotions, creams, or gels. Pharmaceutical preparations may also consist of GHL-Cu, LHG-Cu and derivatives thereof admixed with biologically acceptable materials, such as, for example, polylactic acid, hyaluronic acid, collagen, coral, or hydroxyapitite. These in turn may be incorporated in recognized types of surgical devices used to immobilize and connect fractured or injured bone during the healing process. For example, such surgical devices include pins and plates used to hold fractures together, and artificial joints (e.g., hip) which need to be held in place in the bone. Application of GHL-Cu, LHG-Cu and derivatives thereof may thus be employed at the interface between the device and the bone. The compositions may be used during the initial placement of the device, or may be used if the attachment between the device and the bone subsequently loosens. Various metal ions salts of these biologically acceptable materials may also be used, for example, sodium hyaluronate.

An effective dosage within the pharmaceutical preparations of the present invention comprises about 0.05% to about 5% by weight of GHL-Cu, LHG-Cu and derivatives thereof. A preferred range is about 0.1% to 1.0% by weight.

In another embodiment of the present invention, the pharmaceutical preparation may contain about 0.5% to about 5% by weight of an emulsifying or surface active agent. Non-ionic surface active agents are preferred for the purposes of the present invention. Examples of suitable non-ionic surface active agents are nonylphenoxypolyethoxy ethanol (Nonoxynol-9), polyoxyethylene oleyl ether (Brij-97), various polyoxyethylene ethers (Tritons), and block copolymers of ethylene oxide and propylene oxide of various molecular weights (e.g., Pluronic 68).

Pharmaceutical preparations may also contain about 1% to about 10% by weight of certain ionic surface active agents. These ionic surface active agents may be used in addition to, or in place of, the non-ionic surface active agents. Examples of ionic surface active agents include sodium lauryl sulfate and similar compounds.

In addition to, or in place of, the emulsifying or surface active agent, the pharmaceutical preparation may contain about 1% to about 20% by weight of a penetration enhancing agent. Examples of penetration enhancing agents are dimethyl sulfoxide (DMSO) and urea. In the case of a liquid pharmaceutical preparation to be applied to the bone, the concentration of a penetration enhancing agent such as dimethyl sulfoxide (DMSO) may comprise about 30% to about 80% by weight of the pharmaceutical preparation.

The balance of the pharmaceutical preparation comprises an inert, physiologically acceptable carrier. This carrier should be selected such that it does not substantially interact with the active ingredients, nor reduce the effectiveness of the GHL-Cu, LHG-Cu or derivatives thereof. Suitable carriers include, but are not limited to, water, physiological saline, bacteriostatic saline (saline containing 0.9 mg/ml benzyl alcohol), and petrolatum based creams (USP hydrophilic ointments and similar creams, e.g., Unibase, Parke-Davis).

The following representative pharmaceutical preparations are suitable for use within the methods of the present invention:

| Pharmaceutical Preparation A: | |
|---|---|
| GHL-Cu | 0.4% (w/w) |
| Hydroxyl Ethyl Cellulose | 3.0% |
| Propylene Glycol | 20.0% |
| Nonoxynol-9 | 3.0% |
| Sodium Lauryl Sulfate | 2.0% |
| Benzyl Alcohol | 2.0% |
| 0.2 N Phosphate Buffer | 69.6% |
| Pharmaceutical Preparation B: | |
| GHL-Cu | 0.4% (w/w) |
| Nonoxynol-9 | 3.0% |
| Unibase | 96.6% |
| Pharmaceutical Preparation C: | |
| GHL-Cu | 0.4% (w/w) |
| Bacteriostatic Saline | 30.0 ml |
| Pharmaceutical Preparation D: | |
| GHL-Cu | 0.4% (w/w) |
| Sodium Hyaluronate | 2.0% |
| Sterile Water | 97.6% |
| Pharmaceutical Preparation E: | |
| GHL-Cu | 0.4% (w/w) |
| Hydroxypropyl Cellulose | 2.0% |
| Glycerine | 20.0% |
| Nonoxynol-9 | 3.0% |
| Sterile Water | 74.6% |
| Pharmaceutical Preparation F: | |
| GHL-Cu | 0.4% (w/w) |
| Hydroxypropyl Cellulose | 2.0% |
| Nonoxynol-9 | 3.0% |
| Sterile Water | 94.6% |
| Pharmaceutical Preparation G: | |
| GHL-Cu | 0.4% (w/w) |
| DMSO | 6.0% |
| Unibase | 93.6% |

Administration of the pharmaceutical preparations of the present invention may be accomplished by applying a small amount of the composition directly to the affected bone, such as a fracture, or by injection of the pharmaceutical preparation in the area of the fracture or the area surrounding the fracture, injury, defect or surgical alteration. In essence, any quantity sufficient to accelerate the rate of healing is effective and treatment may be repeated as often as the progress of healing indicates.

Alternative methods of application of the compositions of the present invention include spraying or injecting solutions of GHL-Cu, LHG-Cu and derivatives thereof in acceptable pharmaceutical preparations onto affected bone area, such as the fracture or injured bone and/or the area surrounding the bone during surgical correction procedures. For example, solid or semisolid pharmaceutical preparations containing GHL-Cu, LHG-Cu and derivatives thereof may be implanted at the time of surgical correction of bone fractures. Such pharmaceutical preparations and devices containing GHL-Cu, LHG-Cu and derivatives thereof are implanted near or into the site of fracture or defect to provide a source of GHL-Cu, LHG-Cu and derivatives thereof directly into the area where bone healing is sought.

Similarly, methods of the present invention may also be utilized in the treatment of other hard tissue, such as cartilage, or in the repair of teeth.

As noted above, the compositions of the present invention include GHL-Cu, LHG-Cu or derivatives thereof. The overall chemical reaction in the synthesis of GHL derivatives may be characterized:

$$GHL-OH + R-H \rightarrow GHL-R + H_2O.$$

The reaction is most readily carried out by adding the R group to the amino acid lysine prior to the combination of lysine with the other two amino acids to GHL. After the formation and isolation of GHL-R, the copper(II) is chelated to the molecule to form the bioactive complex.

The overall reaction to form the more lipophilic derivatives of GHL-Cu may be characterized:
1) lysine-OH + R-H → lysine-R + H$_2$O
2) lysine-R + blocked L-histidine → blocked L-histidine-L-lysine-R
3) blocked L-histidine-L-lysine-R → partially blocked L-histidine-L-lysine-R
4) partially blocked L-histidine-L-lysine-R + blocked glycine → blocked glycyl-L-histidine-L-lysine-R
5) blocked glycyl-L-histidine-L-lysine-R → glycyl-L-histidine-L-lysine-R
6) glycyl-L-histidine-L-lysine-R + copper(II) → glycyl-L-histidine-L-lysine-R:copper(II).

The overall reaction to form the more lipophilic derivatives of LHG-Cu is the same as outlined above for GHL-Cu, except glycine-OH is the initial reaction component instead of lysine-OH, and blocked lysine is used in place of blocked glycine in step 4.

To summarize the examples that follow, Example 1 illustrates the synthesis of glycyl-L-histidyl-L-lysine benzyl ester:copper(II). Example 2 demonstrates the synthesis of glycyl-L-histidyl-L-lysine n-octyl ester:copper(II). Example 3 illustrates (A) the synthesis of glycyl-L-histidyl-L-lysine n-stearyl ester:copper(II), and (B) its synthesis by an alternative procedure. Based upon either procedure, one skilled in the art could substitute n-palmityl alcohol (16 carbons) for the n-stearyl alcohol (18 carbons) to yield glycyl-L-histidyl-L-lysine n-stearyl ester:copper(II). Example 4 illustrates (A) the synthesis of glycyl-L-histidyl-L-lysyl-L-prolyl-L-valyl-L-phenylalanyl-L-valine:copper(II) and glycyl-L-histidyl-L-lysyl-L-valyl-L-phenylalanyl-L-valine:copper(II) by solid-phase synthesis, and (B) the preparation of glycyl-L-histidyl-L-lysyl-L-valyl-L-phenylalanyl-L-valine by solution synthesis. Example 7 teaches the addition of copper to the peptides of the present invention. Example 8 illustrates the effectiveness of GHL-Cu, LHG-Cu and derivatives thereof in accelerating the formation of granulation tissue in bone models through the use of representative compositions of the present invention. Examples 9 and 10 illustrate the utility of pharmaceutical preparations containing GHL-Cu, LHG-Cu and derivatives thereof in the healing of bone.

In the following examples, it will be appreciated that, although specific embodiments of the invention will be described herein for purposes of illustration, various modifications may be made without deviating from the spirit and scope of the present invention.

EXAMPLES

Preparation of GHL, LHG, GHL-Cu and LHG-Cu for Use in Animals

GHL and LHG were purified by dissolving, in glass, distilled water (50 mg/ml), then centrifuging at 20,000×g for 1 hour at 3° C. This removes poorly water-soluble material remaining from the synthetic procedure. The supernatant is lyophilized, then passed through a Sephadex G-10 column at 3° C. in a solvent of 0.5% acetic acid. The main peak that elutes behind the solvent front (monitored by absorption at 254 nanometers) is lyophilized to dryness. GHL-Cu and LHG-Cu were prepared by combining purified GHL or LHG with equimolar amounts of cupric acetate and sodium hydroxide, then precipitated by use of ethanol addition and low temperature by published methods (Perkins et al., *Inorg. Chim. Acta* 67:93-99, 1984).

Sources of chemicals. Chemicals and peptide intermediates utilized in the following examples may be purchased from the following suppliers: Sigma Chemical Co. (St. Louis, Mo.); Peninsula Laboratories (San Carlos, Calif.); Aldridge Chemical Co. (Milwaukee, Wis.); Vega Biochemicals (Tucson, Ariz.); Pierce Chemical Co. (Rockford, Ill.); Research Biochemicals (Cleveland, Ohio); Van Waters and Rogers (South San Francisco, Calif.); Bachem, Inc. (Torrance, Calif.).

EXAMPLE 1

Synthesis of glycyl-L-histidyl-L-lysine benzyl ester:copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzylcarbonyl-L-lysine benzyl ester, was coupled to lysine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrifuged at $20,000 \times g$ for 1 hour at 3° C. to remove poorly water-soluble material. The supernatant was lyophilized to obtain glycyl-L-histidyl-L-lysine benzyl ester:copper(II).

EXAMPLE 2

Synthesis of glycyl-L-histidyl-L-lysine n-octyl ester:copper(II)

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anhydrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-L-$N^{im}$-benzyloxy-carbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoracetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonyl-glycine were added to form n-octyl benzyloxycarbonylglycine-$N^{im}$-benzyloxycarbonyl-L-histidyl-$N^e$-benzyloxycarbonyl-L-lysinate. This was dissolved in glacial acetic acid and hydrogenated overnight.

The resultant n-octyl ester of glycyl-L-histidyl-L-lysine was converted to the copper complex by the addition of an equimolar quantity of copper diacetate. The pH was raised to neutrality with sodium hydroxide. The solution was centrifuged at $20,000 \times g$ for 1 hour at 3° C. to remove poorly water-soluble material. The supernatant was lyophilized to obtain glycyl-L-histidyl-L-lysine n-octyl ester:copper(II).

EXAMPLE 3

A. Synthesis of glycyl-L-histidyl-L-lysine n-stearyl ester:copper(II)

A mixture of $N^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl $N^e$-benzyloxycarbonyl-L-lysinate. The product was dissolved in tetrahydrofuran and mixed with $N^a$-t-butyloxycarbonyl-$N^{im}$-benzyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-stearyl $N^{im}$-benzyloxycarbonyl-L-histidyl-$N^e$-benzyloxycarbonyl-L-lysinate, which was dissolved in tetrahydrofuran, isobutyl chloroformate, N-methylmorpholine and benzyloxycarbonyl-glycine to form n-stearyl benzyloxy-carbonylglycyl-$N^{im}$-benzyloxycarbonyl-L-histidyl-$N^e$-benzyloxycarbonyl-L-lysinate. The product was dissolved in 50% trifluoroacetic acid in dichloromethane for 30 minutes, then evaporated, forming n-stearyl ester glycyl-L-histidyl-L-lysine.

The resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ester:copper(II)

$N^e$-benzyloxycarbonyl-L-lysine, n-stearyl alcohol, p-toluenesulfonic acid and monohydrate, and benzene are refluxed together using a Dean-Stark trap to azeotropically remove the evolved water. After cooling to room temperature and then adding dry ethyl ether, n-stearyl $N^e$-benzyloxycarbonyl-L-lysinate p-toluenesulfonate salt is collected by filtration, treated with 2M aqueous potassium bicarbonate solution, and extracted into dichloromethane. Evaporation gives the free amine, which is redissolved in dry tetrahydrofuran (THF) and added to a stirring solution of $N^a$-t-butyloxycarbonyl-$N^{im}$-benzyloxycarbonyl-L-histidine, N-methylmorpholine, and isobutyl chloroformate in dry THF at −15° C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonyl-glycine, N-methylmorpholine and isobutyl chloroformate in dry THF at −15° C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper-complex by the addition of an equimolar quantity of copper diacetate. The pH was raised to neutrality with sodium hydroxide to obtain a produce useful for animal studies.

By substituting n-palmityl alcohol for the n-stearyl alcohol, glycyl-L-histidyl-L-lysine n-palmityl ester may be similarly synthesized.

EXAMPLE 4

A. Solid Phase Synthesis of glycyl-L-histidyl-L-lysyl-L-propyl-L-valyl-L-phenylalanyl-L-valine:copper(II) and of glycyl-L-histidyl-L-lysyl-L-valyl-L-phenylalanyl-L-valine:copper(II)

These peptides are synthesized by standard cold-phase methods common to the peptide field (J. Stewart and J. Young, *Solid Phase Peptide Synthesis*, Pierce Chemical Co., 1984). Briefly stated, Boc-Val-O-Resin was sequentially coupled with other blocked amino acids using dicyclohexylcarbodiimide as a reaction agent. Protected amino acids, resins for solid-phase synthesis, and coupling agents were obtained from Peninsula Laboratories, San Carlos, Calif. Blocked amino acids are added in sequential order to obtain the desired peptide. The final peptide is deblocked using hydrogen fluoride. The final peptide is dissolved in 0.5% acetic acid and purified by passage through a Sephadex G-15 column (Pharmacia). Addition of equimolar cupric acetate, followed by lyophilization, produces the active molecule.

B. Solution Synthesis of glycyl-L-histidyl-L-lysyl-L-valyl-L-phenylalanyl-L-valine Multi-gram quantity of glycyl-L-histidyl-L-lysyl-L-valyl-L-phenylalanyl-L-valine was synthesized by standard solution phase method using t-butyloxycarbonyl protecting group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, $N^a$-t-butyloxycarbonyl-$N^e$-benzyloxycarbonyl-L-lysine, $N^a$-t-butyloxycarbonyl-$N^{im}$-benzyloxycarbonyl-L-histidine, benzyloxycarbonyl-glycine) were added in sequential order to obtain the desired peptide. The final peptide was lyophilized from water and purified by liquid chromatography on a C-18 reverse-phase column to produce the desired hexapeptide in multigram quantity.

EXAMPLE 5

Synthesis of L-lysyl-L-histidyl-glycine $N^a$-t-butyloxycarbonyl-$N^{im}$-benzyloxycarbonyl-L-histidine was dissolved in tetrahydrofuran (THF) and neutralized with one equivalent of N-methylmorpholine. It was then coupled with benzyl glycinate p-toluenesulfonate salt using isobutyl chloroformate and N-methylmorpholine. After two hours at −20° C. and an additional hour at ambient temperature, the reaction was quenched with 2N aqueous potassium bicarbonate. The product was extracted into ethyl acetate, washed first with 1M aqueous citric acid, and second with saturated sodium bicarbonate. The organic phase was dried over anhydrous sodium sulfate. Filtration and evaporation gave benzyl $N^a$-t-butyloxycarbonyl-$N^{im}$-benzyloxycarbonyl-L-histidyl-glycinate.

This product was dissolved in anhydrous methanolic hydrogen chloride (saturated at 0° C.) for 5 minutes, followed by removal of solvent under reduced pressure, forming benzyl $N^{im}$-benzyloxycarbonyl-L-histidyl-glycinate. This was dissolved in tetrahydrofuran, and isobutyl chloroformate, N-methylmorpholine and $N^a,N^e$-dibenzyloxycarbonyl-L-lysine were added to form benzyl $N^a,N^e$-dibenzyloxycarbonyl-L-lysyl-L-histidyl-glycinate (3 hours at −20° C., then 1 hour at ambient temperature). This product was then dissolved in methanol/acetic acid [1:1 (v/v)] and hydrogenated overnight in the presence of 10% Pd-C catalyst. The resultant L-lysyl-L-histidyl-glycine was lyophilized from water several times, then purified by liquid chromatography on a C-18 reverse phase column to yield the desired tripeptide triacetate salt as a foamy white solid.

EXAMPLE 6

Synthesis of L-lysyl-L-histidyl-glycyl-L-valyl-L-phenylalanyl-L-valine

Multi-gram quantity of L-lysyl-L-histidyl-glycyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agents (2 hours at $-20°$ C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, t-butyloxycarbonyl-glycine, $N^\alpha$-t-butyloxycarbonyl-$N^{im}$-benzyloxycarbonyl-L-histidine, $N^\alpha,N^\epsilon$-dibenzyloxycarbonyl-L-lysine) were added in sequential order to obtain the desired peptide. The final peptide was completely deprotected using hydrogen gas in glacial acetic acid for 5 days in the presence of 10% Pd-C catalyst. The final peptide was lyophilized from water and purified by liquid chromatography on a C-18 reverse-phase column to produce the desired hexapeptide in multi-gram quantity.

The above systematic synthesis proved advantageous over some of the solid-phase methods in providing multi-gram quantity of the desired peptide in high purity with minimal purification.

EXAMPLE 7

Preparation of GHL-Cu, LHG-CU and Derivatives Thereof

Purified GHL-Cu, LHG-Cu and derivatives thereof can be prepared in any molar ratio by the addition of a required molar amount of ultrapure cupric chloride (Ultralog 99.999% available from Chemical Dynamics, N.J., for example) to the glycyl-L-histidyl-L-lysine, or lysyl-L-histidyl-L-glycine or derivatives thereof in solution in distilled water. After the addition of the cupric chloride, the pH of the solution is adjusted to approximate neutrality. Any precipitate formed can be removed by centrifugation and filtration by methods known in the art.

EXAMPLE 8

Effect of GHL-Cu, LHG-Cu and Derivatives Thereof on the Formation of Granulation Tissue in Bone Models Implanted in Rats The subcutaneous implantation of stainless steel chambers in rats provides a reproducible models to monitor the healing of bone. This model in many ways mimics the early events in the formation of granulation tissue found in fractures or other types of injury to bone. Implantation of these chambers triggers a series of responses which reflect the series of phases involved in bone healing—fibrin clot formation, infiltration of white cells, collagen synthesis, and new blood vessel formation.

The assay involves the implantation of two stainless steel chambers (1×2.5 cm cylindrical 312 SS, 20 mesh, with Teflon end caps) on each side of the dorsal midline of rats. After one week to allow for encapsulation of the chambers, one chamber on each rat was injected with 0.2 ml of a 10 mg/ml solution of GHL-Cu and the other with the same volume of saline. Injections are made on days 5, 7, 8, 12, 13, 15 and 19. The chambers were removed on day 15 and day 29.

The chambers were lyophilized and the interior contents removed for biochemical analysis. The biochemical parameters examined include the total dry weight, protein content, angiogenesis (alkaline phosphatase activity), and collagen content (hydroxyproline content after acid hydrolysis). Significant increases were found in all the biochemical parameters tested when compounds of the present invention were used as compared to controls.

Protein content was determined by the method of Lowry (Lowry et al., *J. Biol. Chem.* 193:265-275, 1951) using Bovine Serum Albumin (BSA) as a standard. Angiogenesis was determined by measuring the amount of alkaline phosphatase activity using p-nitrophenyl phosphate as a substrate (Lyles et al., *C. Biochem. Pharm.* 33:2569-2574, 1984). The collagen content was determined by acid hydrolysis and a colorimetric assay for hydroxyproline (Bergman et al., *R. Clin. Chim. Acta* 27:347-349, 1970), an amino acid specific for collagen.

The total protein is expressed as mg protein (relative to BSA) per chamber, the angiogenesis as alkaline phosphatase (AP) units per chamber, where one unit=the amount of homogenate which causes an increase in absorbance at 405 nm of 1.0 per min., and the hydroxyproline (HP, Collagen Content) as $\mu$g HP per chamber. Comparison with control data is made by determining the ratio, treated/control (T/C) for each parameter.

A summary of the data is shown in Table 1. Graphs showing the comparison data are included as FIGS. 1-4. Differences in the chamber dry weight and total protein content were evident at both days 15 and 29, with the maximal T/C ratios ($\sim$2) at day 15. In contrast, there were no detectable differences in either angiogenesis or collagen content on day 15. By day 29, however, there were significant differences in both angiogenesis (T/C=3.2) and collagen (T/C=1.9) content of the chambers.

TABLE 1

| | EFFECT OF GHL-Cu ON GRANULATION TISSUE FORMATION IN A BONE HEALING MODEL | | | |
|---|---|---|---|---|
| DAY | DRY WEIGHT mg | PROTEIN mg/chamber | COLLAGEN $\mu$g HP/chamber | ANGIOGENESIS AP units/chamber |
| CONTROL DAY 15 | 42 ± 14 | 34 ± 9 | 183 ± 216 | 6.2 ± 1.8 |
| GHL-Cu | 92 ± 46 | 69 ± 32 | 243 ± 215 | 6.5 ± 3.2 |
| T/C = | [2.2] | [2.0] | [1.1] | [1.0] |
| CONTROL DAY 29 | 95 ± 32 | 56 ± 18 | 978 ± 644 | 6.4 ± 5.0 |
| CHL-Cu | 165 ± 38 | 77 ± 19 | 1849 ± 546 | 20.3 ± 10.0 |

TABLE 1-continued

EFFECT OF GHL-Cu ON GRANULATION TISSUE FORMATION
IN A BONE HEALING MODEL

| DAY | DRY WEIGHT mg | PROTEIN mg/chamber | COLLAGEN μg HP/chamber | ANGIOGENESIS AP units/chamber |
|---|---|---|---|---|
| T/C = | [1.7] | [1.4] | [1.9] | [3.2] |

EXAMPLE 9

Healing of Bone by Compositions of the Present Invention

GHL-Cu, LHG-Cu and derivatives thereof have shown bone healing activity. In one representative study, male rats weighing approximately 350–400 grams received drill holes in bone which were then treated with pharmaceutical preparations containing GHL-Cu.

More specifically, on the day of surgery (Day 0), animals were sedated with pentobarbital (I.P., 35 mg/kg). The hair was clipped from the left rear upper limb, and the area was prepped in a sterile fashion. Using a #15 blade, a 2 cm incision was made on the lateral surface of the upper limb following the approximate location of the femur, extending from just below the crest of the ilium. The tensor fasciae latae muscle was exposed and incised parallel to the muscle filers (1 cm incision). Careful retraction of the muscle provided exposure of the vastus lateralis muscle overlying the femur. The approach to the femur was completed upon incision and retraction of this muscle. This provided exposure of 1 cm of the lateral and ventral surfaces of bone. Using a periosteal elevator, the surface of the femur was cleaned of periosteum. At this point, very little bleeding had been encountered. Using a Dremel drill fitted with a 1 mm diameter cutting burr, a hole was drilled in the femur to a depth of approximately 0.75 mm. Little bleeding was evident except in the rare case of marrow penetration. The area was irrigated and hemostasis achieved. At this point, a pharmaceutical preparation of the compositions of the present invention was applied to the exposed bone surface. The muscle was closed in layers using chromic suture, and the skin was closed with stainless steel wound clips. Structure and function of the muscles was intact following surgery, and very little, if any, morbidity was associated with the surgical procedure.

After 7 to 14 days, the animals were terminated and their femurs removed. Evidence of bone growth was determined from gross visualization of the defect using a Wild dissecting scope, and from subsequent histological preparations (decalcification, paraffin embedding, and Trichrome staining).

Results at 12 to 14 days following surgery utilizing pharmaceutical preparation B to accelerate the bone healing process are summarized in Table 2. Controls consisted of bones without treatment. Visual inspection revealed no filling of the created defect (−), or filling (+) with soft or moderately soft material. Microscopic examination (micro) revealed the filling percentage of the defect.

TABLE 2

| Animal # | Rx | Visual (+/−) | Micro (% Filled) |
|---|---|---|---|
| 10311 | 1 | + (soft) | 100 |
| 10312 | 1 | − | not readable |
| 10313 | 2 | − | not readable |
| 10314 | 2 | − | not readable |
| 10315 | 1 | + (soft) | 80 |

TABLE 2-continued

| Animal # | Rx | Visual (+/−) | Micro (% Filled) |
|---|---|---|---|
| 10316 | 2 | + (mod. soft) | 20 |
| 10317 | 1 | − | not readable |
| 10318 | 2 | − | 0 |
| 10346 | 1 | + (mod. soft) | 100 |

Treatment (Rx)
1 = Pharmaceutical Preparation B
2 = Control, no treatment

Those in which the marrow had been entered by the drill bit appeared to develop soft to moderate soft tissue in the created defect (one/treatment group). Tissue was observed more frequently in treated bones.

EXAMPLE 10

Healing of Bone by Compositions of the Present Invention Within Pharmaceutical Gels In a second study, defects were created in bones and pharmaceutical preparation E applied to the exposed bone in the same manner as described in Example 9. Results at days 7 and 14 are given in Table 3.

TABLE 3

| Animal # | Rx | Day | Visual (+/−) | Micro (% Filled) |
|---|---|---|---|---|
| 10445 | 1 | 7 | − | 0 |
| 10449 | 1 | 7 | − | 0 |
| 10456 | 1 | 14 | + | 25 |
| 10457 | 1 | 14 | − | 0 |
| 10443 | 2 | 7 | + | 100 |
| 10451 | 2 | 7 | + | 80 |
| 10458 | 2 | 14 | + (soft) | 50 |
| 10459 | 2 | 14 | + | 25 |

Treatments (Rx)
1 = Placebo Gel
2 = Pharmaceutical Preparation E

Figure 1:
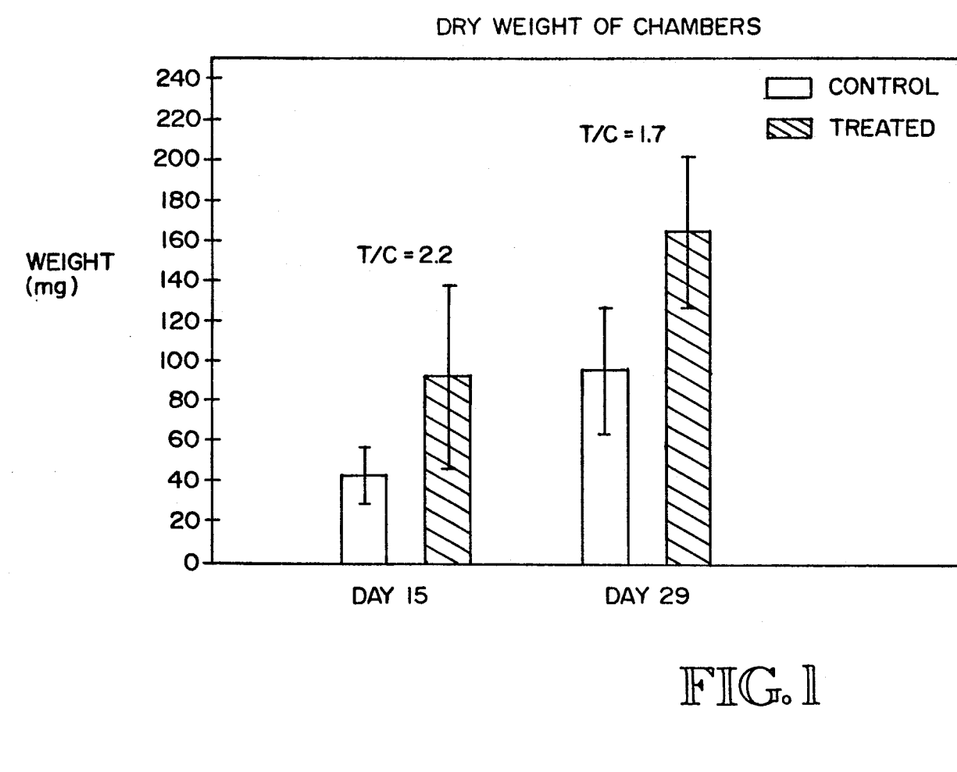
FIG. 1 graphically illustrates the increase in the dry weight of a bone model through use of a representative composition of the present invention.
Figure 2:
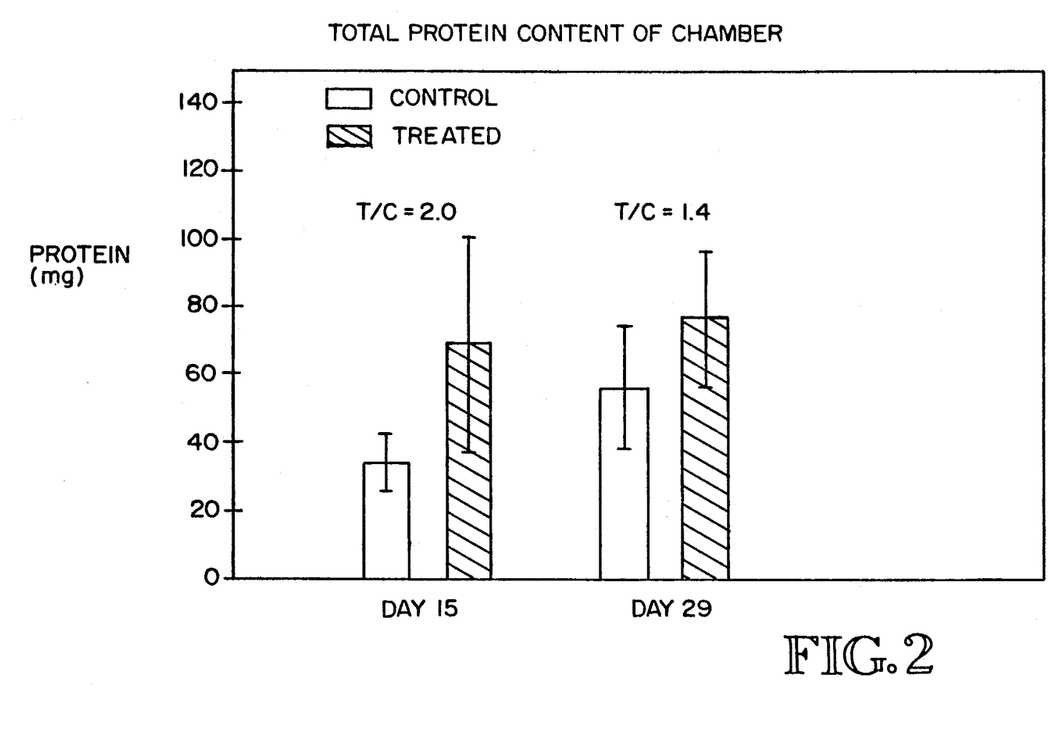
FIG. 2 graphically depicts the stimulation of a bone model through use of a representative composition of the present invention.
Figure 3:
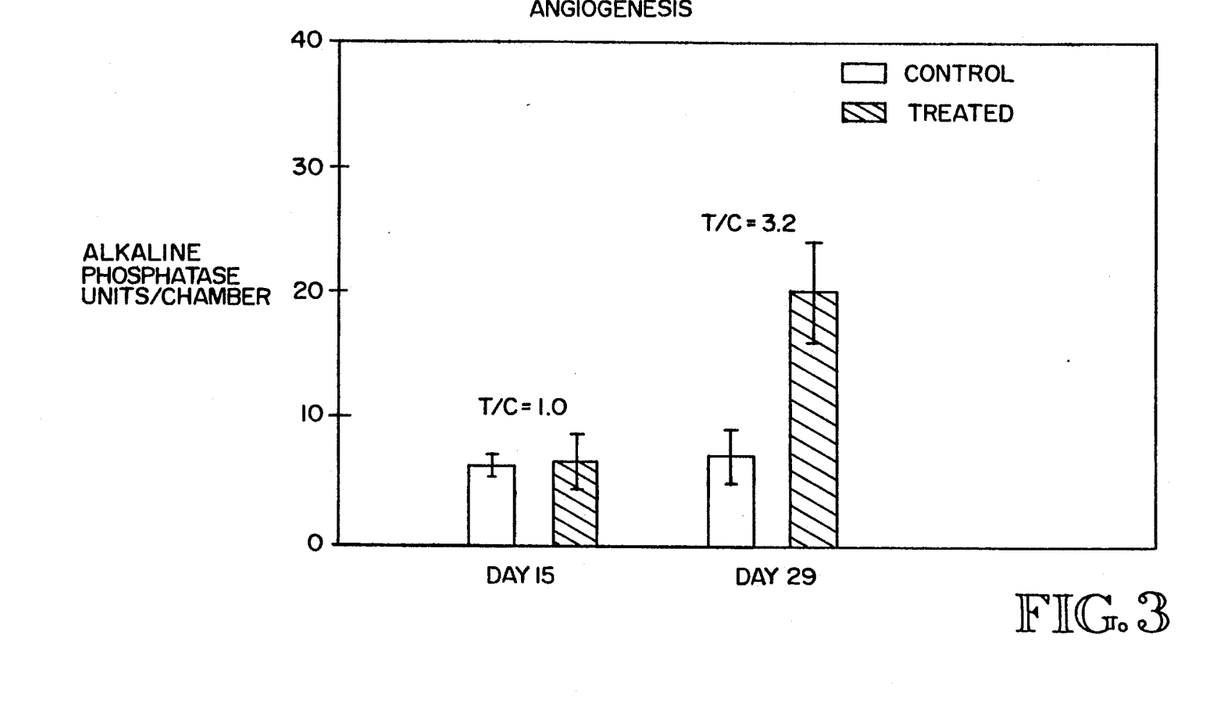
FIG. 3 graphically illustrates the stimulation of angiogenesis in a bone model through use of a representative composition of the present invention.
Figure 4:
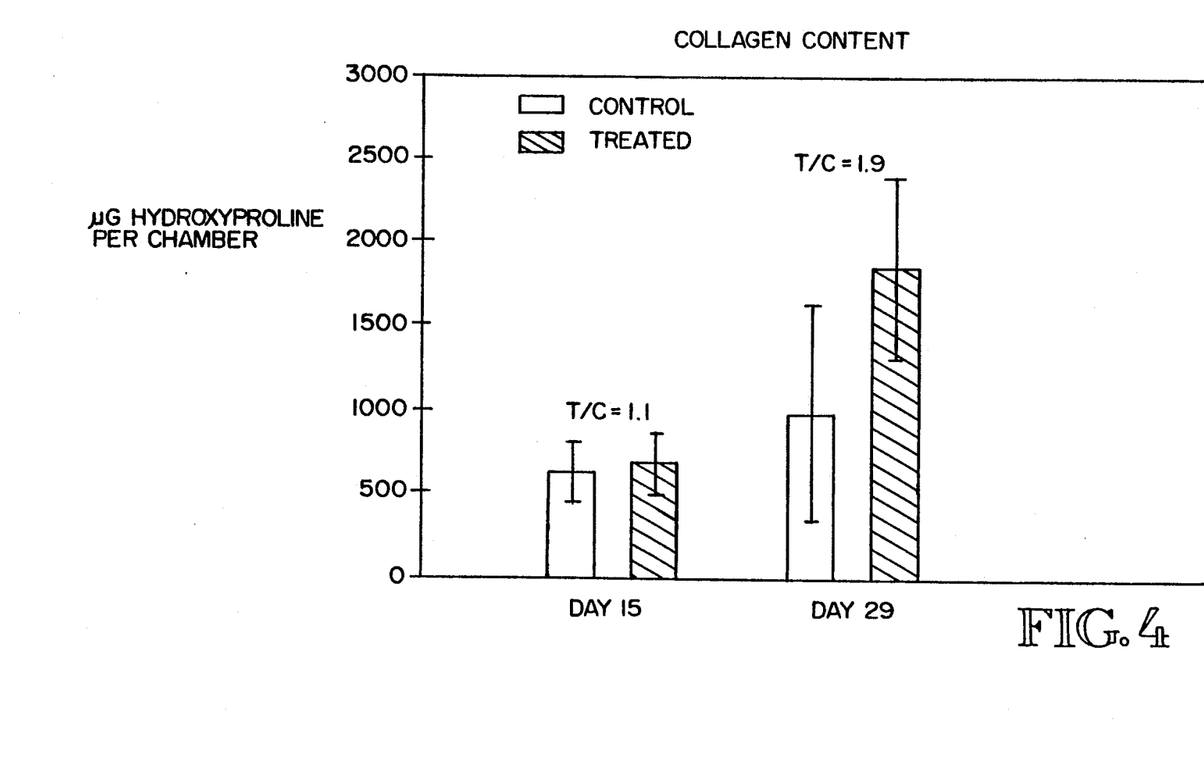
FIG. 4 graphically depicts the stimulation of collagen synthesis in a bone model through use of a representative composition of the present invention.
Figure 5A:
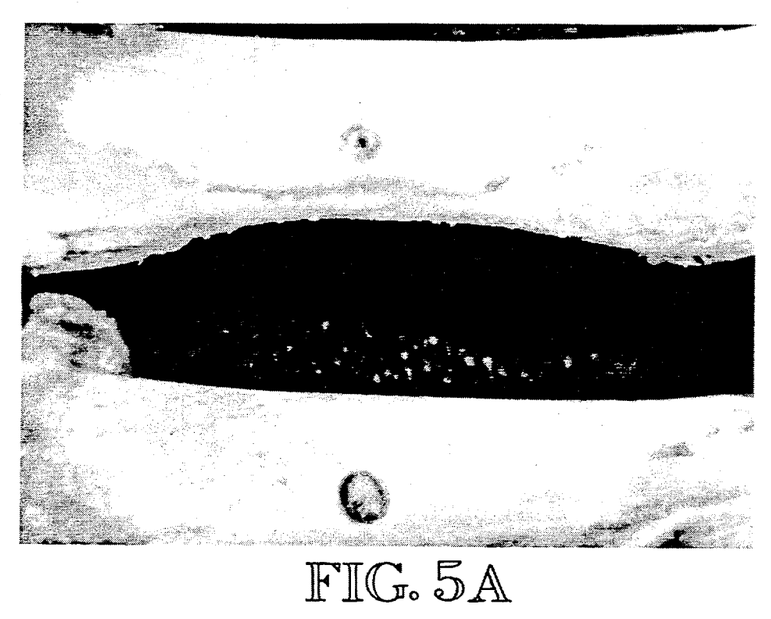
FIG. 5 is set of three photographs illustrating the healing of untreated bone defects and bone defects treated with representative compositions of the present invention.
Figure 5B:
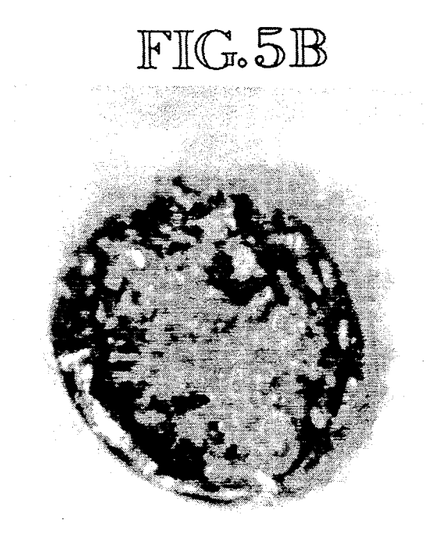
Figure 5C:
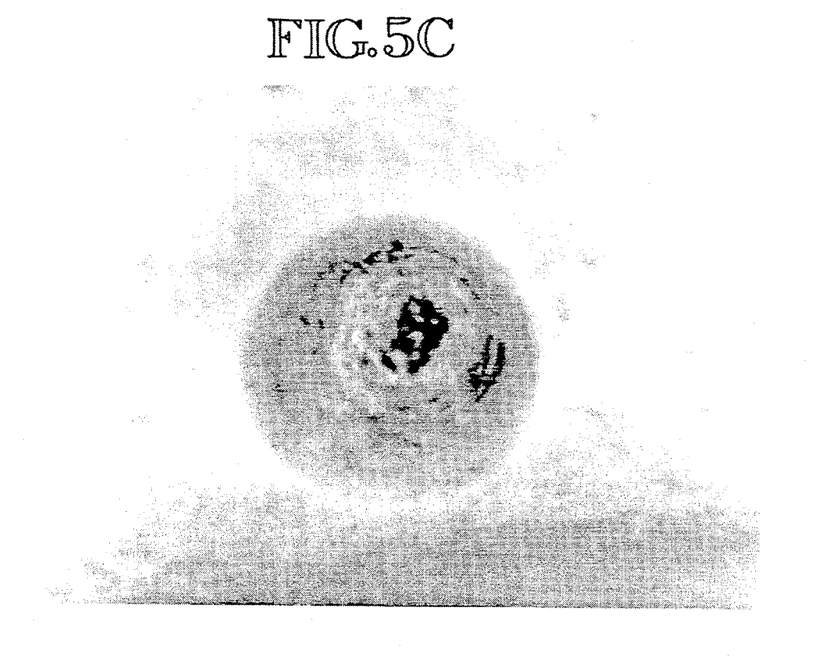

Visual examples of treated amd placebo-gel-treated bone defects are shown in FIG. 5. Two bones are shown at day 7 in FIG. 5A, with the treated bone on the left and the control on the right. FIG. 5C is a close-up photograph of the placebo gel-treated bone, and FIG. 5A is a photograph of GHL-Cu-treated bone showing influx of bony calcification and granulation tissue. GHL-Cu-treated bone specimens contain varying amounts of hard, vascularized bone extruding from the core (marrow). The control specimens generally have less filling, and of a softer, fibrous nature.

Figures 6A, 6B:
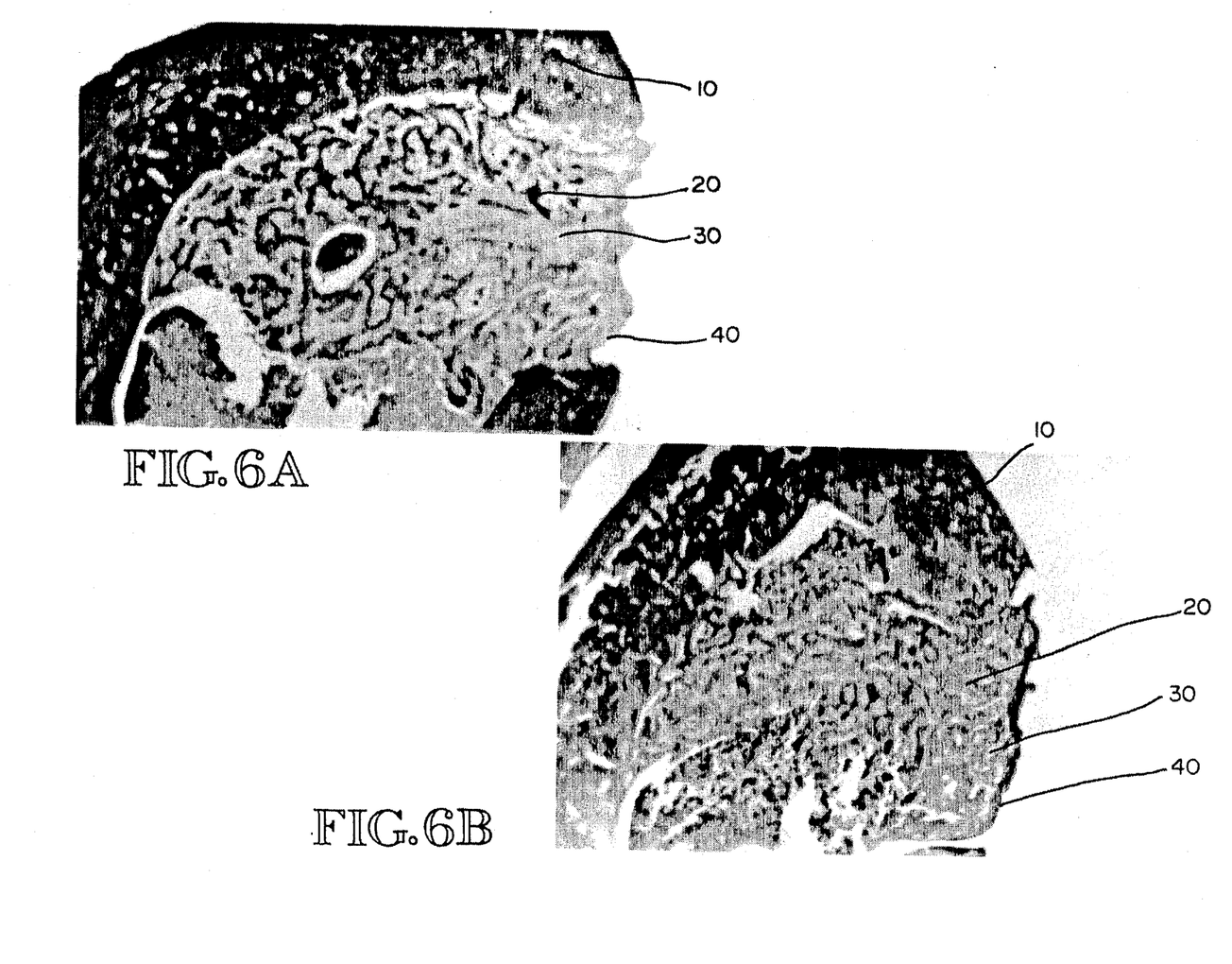
FIG. 6 is a pair of micrographs of bone defects treated with placebo and representative compositions of the present invention.

FIG. 6 is a pair of photomicrographs of placebo (FIG. 6A) and GHL-Cu-treated bone (FIG. 6B), X40, Trichrome stain. The periosteal layer (40) is better developed and continuous in the GHL-Cu specimens (FIG. 6B) than the placebo-treated bone (FIG. 6A). In addition, interanastomosing islands of new (woven) bone (20) are observed in FIG. 6B. Also, the intertrabecullar spaces (30) in FIG. 6B are filled with adipocytes and vascular channels, as seen in mature bone. Moreover, there is less communication between the intertrabecullar spaces in the GHL-Cu-treated bone, indicating a firmer consistency. Existing bone (10) surrounds the affected bone area.

The treatment period of 7 days allowed for a differentiation between the treated and control bone when examined histologically and grossly. The composition of the present invention stimulated bone growth more rapidly than the control.

Figure 7A:
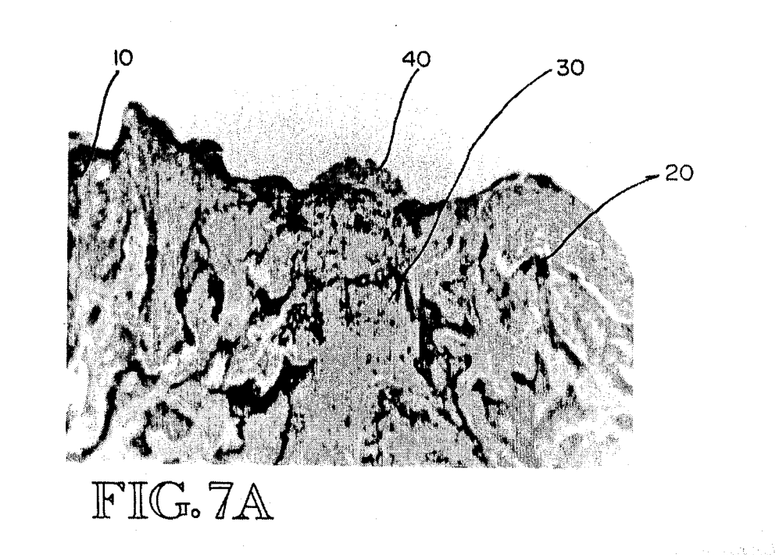
FIG. 7 is pair of micrographs of placebo and treated bone defects at a higher magnification than FIG. 6.
Figure 7B:
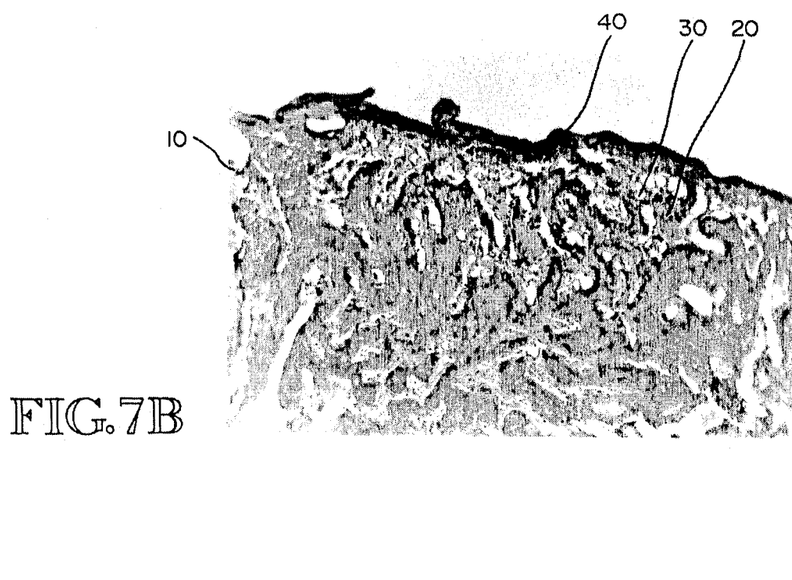

FIG. 7 is a pair of photomicrographs of placebo (FIG. 7A) and GHL-Cu-treated (FIG. 7B) bone defects, X 63, Trichrome stain. An increase in density of new bone (20) and general increased tissue density and aggregation of bone cells in the GHL-Cu-treated defect is seen in FIG. 7B. Intertrabecullar space (30), the periosteal layer (40), and existing bone (10) are readily identified.

These results demonstrate that treatment with compositions of the present invention increased the healing of the affected bone, induced the formation of granulation tissued in affected bone, and accelerated the formation of new bone growth in the affected bone.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for promoting the healing of affected bone in warm-blooded animals, comprising:
   administering to an affected bone or the area surrounding the affected bone a therapeutically effective amount of a composition containing glycyl-L-histidyl-L-lysine:copper (II).

2. A method for promoting the healing of affected bone in warm-blooded animals, comprising:
   administering to an affected bone or the area surrounding the affected bone a therapeutically effective amount of a composition containing L-lysyl-L-histidyl-glycine:copper (II).

3. A method for promoting the healing of affected bone in warm-blooded animals, comprising:
   administering to an affected bone or the area surrounding the affected bone a therapeutically effective amount of a composition containing a derivative of GHL-Cu having the general formula:

wherein R is selected from the group consisting of an -NH$_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine, L-valyl-L-phenylalanyl-L-valine, L-tryptophan, or (glycyl)$_n$-L-tryptophan, where n=1-2.

4. A method for accelerating the healing of affected bone in warm-blooded animals, comprising:
   administering to an affected bone or the area surrounding the affected bone a therapeutically effective amount of a composition containing a derivative of GHL-Cu having the general formula:

wherein R is selected from the group consisting of an -NH$_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine, L-valyl-L-phenylalanyl-L-valine, L-tryptophan, or (glycyl)$_n$-L-tryptophan, where n=1-2.

5. A method for inducing the formation of granulation tissue in affected bone in warm-blooded animals, comprising:
   administering to an affected bone or the area surrounding the affected bone a therapeutically effective amount of a composition containing glycyl-L-histidyl-L-lysine:copper (II).

6. A method for inducing the formation of granulation tissue in affected bone in warm-blooded animals, comprising:
   administering to an affected bone or the area surrounding the affected bone a therapeutically effective amount of a composition containing L-lysyl-L-histidyl-glycine:copper (II).

7. A method for inducing the formation of granulation tissue in affected bone in warm-blooded animals, comprising:
   administering to an affected bone or the area surrounding the affected bone a therapeutically effective amount of a composition containing a derivative of GHL-Cu having the general formula:

wherein R is selected from the group consisting of an -NH$_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine, L-valyl-L-phenylalanyl-L-valine, L-tryptophan, or (glycyl)$_n$-L-tryptophan, where n=1-2.

8. A method for inducing the formation of granulation tissue in affected bone in warm-blooded animals, comprising:
   administering to an affected bone or the area surrounding the affected bone a therapeutically effective amount of a composition containing a derivative of GHL-Cu having the general formula:

wherein R is selected from the group consisting of an -NH$_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine, L- valyl-L-phenylalanyl-L-valine, L-tryptophan, or (glycyl)$_n$-L-tryptophan, where n=1–2.

9. A method for accelerating the formation of new bone growth associated with an artificial device implanted in bone in warm-blooded animals, comprising:
administering to the area of the bone implanted with the artificial device a therapeutically effective amount of a composition containing glycyl-L-histidyl-L-lysine:copper (II).

10. A method for accelerating the formation of new bone growth associated with an artificial device implanted in bone in warm-blooded animals, comprising:
administering to the area of the bone implanted with the artificial device a therapeutically effective amount of a composition containing L-lysyl-L-histidyl-glycine:copper (II).

11. A method for accelerating the formation of new bone growth associated with an artificial device implanted in bone in warm-blooded animals, comprising:
administering to the area of bone implanted with the artificial device a therapeutically effective amount of a composition containing a derivative of GHL-Cu having the general formula:

[glycyl—L—histidyl—L—lysine—C(=O)—R]:copper(II)

wherein R is selected from the group consisting of an -NH$_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine, L-valyl-L-phenylalanyl-L-valine, L-tryptophan, or (glycyl)$_n$-L-tryptophan, where n=1–2.

12. A method for accelerating the formation of new bone growth associated with an artificial device implanted in bone in warm-blooded animals, comprising:
administering to the area of bone implanted with the artificial device a therapeutically effective amount of a composition containing a derivative of GHL-Cu having the general formula:

[L—lysyl—L—histidyl—glycine—C(=O)—R]:copper(II)

wherein R is selected from the group consisting of an -NH$_2$ moiety, alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine, L-valyl-L-phenylalanyl-L-valine, L-tryptophan, or (glycyl)$_n$-L-tryptophan, where n=1–2.

13. The method of any one of claims 1–12 wherein the composition includes a penetration enhancing agent.

14. The method of any one of claims 1–12 wherein the composition includes a surface active agent.

15. The method of any one of claims 1–12 wherein the composition is administered by direct application to the bone.

16. The method of any one of claims 1–12 wherein the composition includes collagen.

* * * * *